United States Patent [19]

Lippman

[11] 4,025,586

[45] May 24, 1977

[54] PREPARATION OF DIALKYL PHOSPHOROCHLORIDOTHIOATES

[75] Inventor: Alfred E. Lippman, Creve Coeur, Mo.

[73] Assignee: Monsanto Company, St. Louis, Mo.

[22] Filed: Apr. 21, 1976

[21] Appl. No.: 678,803

[52] U.S. Cl. .................................. 260/986; 260/990
[51] Int. Cl.² ........................................... C07F 9/20
[58] Field of Search ........................... 260/986, 990

[56] References Cited

UNITED STATES PATENTS

| | | | |
|---|---|---|---|
| 3,502,750 | 3/1970 | Anglaret et al. .................... | 260/986 |
| 3,794,703 | 2/1974 | Beck et al. ......................... | 260/990 |
| 3,836,610 | 9/1974 | Diveley .............................. | 260/986 |
| 3,856,898 | 12/1974 | Diveley .............................. | 260/990 |
| 3,897,523 | 7/1975 | Sorstokke .......................... | 260/986 |

FOREIGN PATENTS OR APPLICATIONS 1,245,052  9/1971  United Kingdom

*Primary Examiner*—Richard L. Raymond
*Attorney, Agent, or Firm*—Richard H. Shear; Donald W. Peterson

[57] ABSTRACT

This invention relates to a method of preparing dialkyl phosphorochloridothioates in which unconverted bis-(thiophosphono)sulfide is washed and returned to the chlorinator.

2 Claims, 1 Drawing Figure

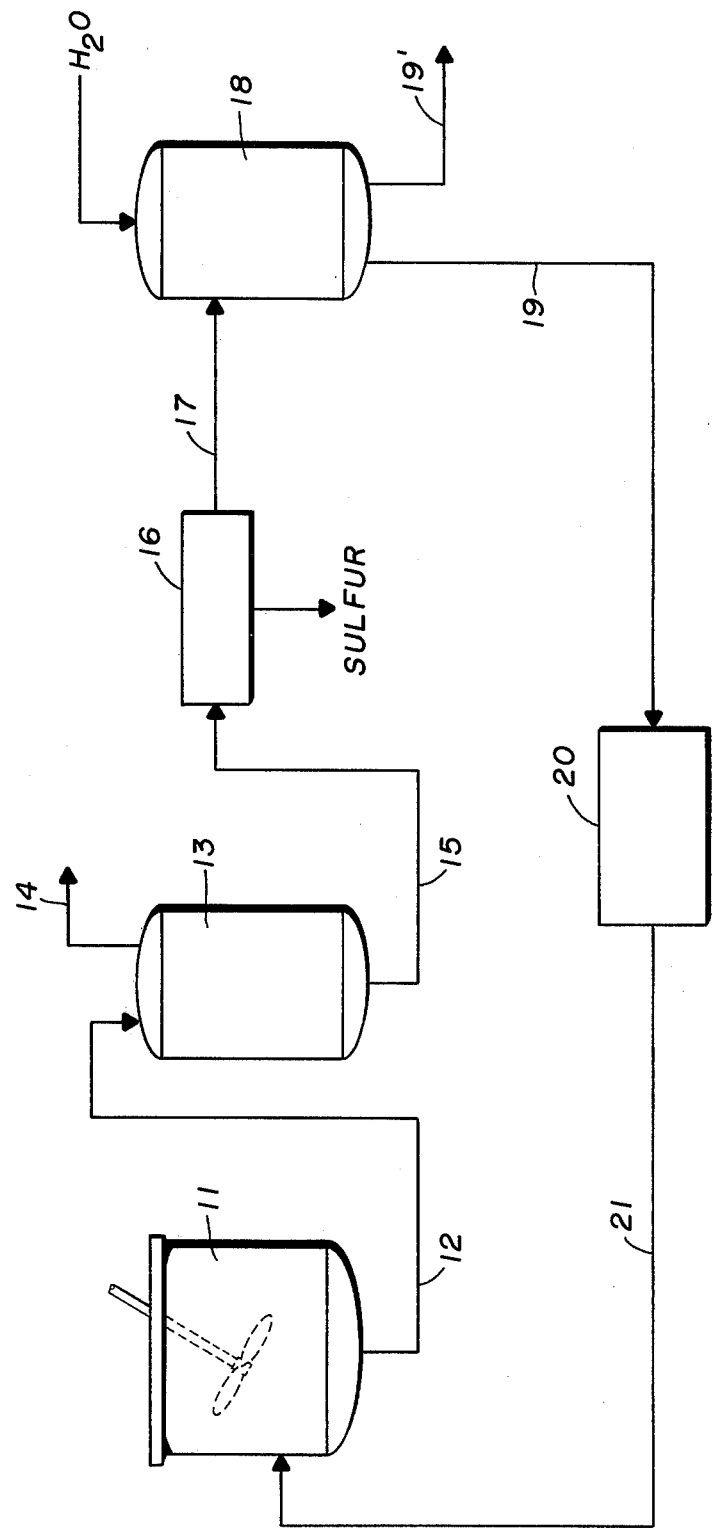

PREPARATION OF DIALKYL PHOSPHOROCHLORIDOTHIOATES

This invention relates to the preparation of dialkyl phosphorochloridothioates having the structure

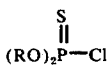

wherein R is alkyl. The dialkyl phosphorochloridothioates are useful as intermediates in the manufacture of pesticides.

Generally, dialkyl phosphorochloridothioates are prepared by chlorinating dialkyl phosphorodithioic acid. This reaction proceeds according to equation I

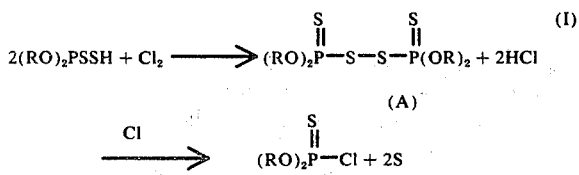

High yields of dialkyl phosphorochloridothioate have not been attainable without providing sufficient chlorine to convert most of the bis(thiophosphono)sulfide intermediate (A). Such conversion levels, however, result in a distillation residue that is thermally unstable and potentially dangerous. It has been the practice, therefore, to utilize less chlorine, leaving rather large amounts of the bis(thiophosphono)sulfide intermediate, (A), unconverted. After distillation, the unconverted intermediate has usually been incinerated, emitting $SO_2$ to the atmosphere.

The present invention provides a method of preparing dialkyl phosphorochloridothioate in high yields without thermally unstable distillation residues.

It is therefore an object of the invention to provide a method for the preparation of dialkyl phosphorochloridothioate in high yields.

A second object of the invention is to provide a method for the preparation of dialkyl phosphorochloridothioates witout wasting large quantities of the bis(thiophosphono)sulfide intermediate.

A further object of the invention is to provide a method for the preparation of dialkyl phosphorochloridothioate that eliminates the need to incinerate the reaction by-products resulting in $SO_2$ emissions to the atmosphere These and other objects of the invention may be accomplished by chlorinating dialkyl phosphorodithioic acid in accordance with Equation I above. Distillation provides a distillate consisting essentially of dialkyl phosphorochloridothioate and a distillation residue containing unreacted bis(thiophosphono)sulfide intermediate, small amounts of dialkyl phosphorochloridothioate, various impurities and sulfur. In accordance with the process of the invention the distillation residue is purified and recycled.

In order to better illustrate the process of the invention, the FIGURE, representing a flow diagram of the process, is provided. Dialkyl phosphorodithioic acid is chlorinated in chlorinator 11. The reaction mixture 12 is fed to still 13 where distillation provides a distillate 14 consisting essentially of dialkyl phosphorochloridothioate and a residue 15 consisting essentially of bis(thiophosphono)sulfide, a small amount of dialkyl phosphorochloridothioate, sulfur and several impurities. Solid elemental sulfur may then be removed by known means, e.g. centrifuge 16. The remaining residue is then sent through a water wash 18 where most of the impurities are removed by selective hydrolysis. By the term "selective hydrolysis" is meant the hydrolysis of those hydrolyzable impurities without hydrolyzing the bis(thiophosphono)sulfide intermediate. After separating the hydrolyzed impurities 19', the washed residue 19 is dried in drier 20. The dried liquid residue 21 consists essentially of the bis(thiophosphono)sulfide intermediate. The residue additionally may contain a small amount of dialkyl phosphorochloridothioate, as well as dissolved sulfur and other non-hydrolyzable impurities. The amounts of these impurities in the residue quickly reach steady state at rather low levels as they are removed during the water wash or distillation. After drying, the residue is returned to the chlorinator.

The prior art has suggested the use of the distillation residue as an additional feed material for the chlorination of a further amount of dialkyl phosphorodithioic acid. British Pat. No. 1,245,052 discloses such a process. Said patent states, however, that the residue consists substantially of sulfur. After removing the sulfur, the residue is immediately available for use in the chlorination of dialkyl phosphorodithioic acid.

It has been found that recycling of the distillation residue after removing elemental solid sulfur, but without water washing, causes the hydrolyzable impurities to accumulate and ultimately decompose and polymerize. The polymerized impurities quickly build up, have a glue-like consistency and interfere with the desired chlorination.

By washing the residue 17 with water the impurities are hydrolyzed and can be removed. It is important that the hydrolysis not proceed at rates sufficient to hydrolyze the bis(thiophosphono)sulfide intermediate. Accordingly, it has been found that a wash for less than one hour at temperatures below 50° C. provides such a selective hydrolysis. It is well within the skill of the art to vary the temperature or the residence time to prevent hydrolysis of the bis(thiophosphono)sulfide. Since the hydrolysis is exothermic, a simple way in which to monitor said hydrolysis is to begin washing at room temperature and continue until the exotherm has subsided.

As noted previously, the washed residue 19 must be dried. It is important that the residue be dried such that the water remaining in said residue be below about 2 percent by weight and preferably below about 0.3 percent. If too much water is allowed to remain in the residue, hydrolysis in the chlorinator of dialkyl phosphorodithioic acid to dialkyl phosphoric acid may occur, causng a decrease in yield.

Typically, the amount of chlorine required is that which will react with all of the dialkyl phosphorodithioic acid present. This amount can be readily determined by varying the amount of chlorine after each batch until the amount of washed and dried liquid still residue being returned to the chlorinator is equal to the amount that was previously used.

Table I is provided to illustrate the benefits of the invention. Example 1 is indicative of the yield of dimethyl phosphorochloridothioate prepared according to known processes. Example 2 is indicative of the yield of dimethyl phosphorochloridothioate prepared in accordance with the process of the invention.

TABLE I

| | CHARGE | | | DISTILLATION | | | |
|---|---|---|---|---|---|---|---|
| | Dimethyl Phosphorodithioic Acid | Chlorine | Washed & Dried Lqd. Residue | Crude Product | Dimethyl Phosphorochloridothioate | Residue | Yield* |
| Example 1 | 80 parts | 33 parts | | 97 | 65 | 32[2] | 80% |
| Example 2 | 58 parts | 25.2 parts | 22 parts[1] | 93.7 | 51.4 | 42.3[3] | 90% |

*Based on dimethyl phosphorodithioic acid
[1] Consists of bis(thiophosphono)sulfide itermediate and dissolved sulfur from the previous batch
[2] Consists of approximately
  - 2.5 dimethyl phosphorochloridothioate
  - 6.0 bis(thiophosphono)sulfide intermediate
  - 4.5 elemental solid sulfur
  - 9.0 dissolved sulfur
  - 10.0 impurities

[3] Consists of approximately
  - 2.0 dimethyl phosphorochloridothioate
  - 12.0 bis(thiophosphono)sulfide intermediate
  - 10.6 elemental solid sulfur
  - 10.0 dissolved sulfur
  - 7.7 impurities The table illustrates that when prepared in accordance with the present invention, the yield of dimethyl phosphorochloridothioate can be increased by 10 percent. Washing and drying of the distillation residue will remove all but the 12 parts of bis(thiophosphono)sulfide and 10 parts of dissolved sulfur which can then be recycled back to the chlorinator.

As is readily apparent, the amount of dialkyl phosphorodithioic acid required can be dramatically reduced when dialkyl phosphorochloridothioates are prepared in accordance with the present invention. Additionally, no by-products of streams need be incinerated.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. In a method for the preparation of dialkyl phosphorochloridothioate which comprises chlorinating dialkyl phosphorodithioic acid in a reaction vessel to yield a reaction mixture comprising said dialkyl phosphorochloridothioate, bis(thiophosphono)sulfide intermediate, sulfur and impurities associated with said chlorination and distilling said reaction mixture to provide a distillate consisting essentially of said dialkyl phosphorochloridothioate and a distillation residue comprising said bis(thiophosphono)sulfide intermediate, sulfur and said impurities; the improvement which comprises
   a. removing solid sulfur from said distillation residue;
   b. washing the remaining residue with water to selectively hydrolyze said impurities;
   c. removing from said residue said selectively hydrolyzed impurities;
   d. drying said washed residue such that its water content is below about 2 percent by weight; and
   e. recycling said dried residue to said reaction vessel.

2. A method according to claim 1 wherein said residue is dried such that its water content is below 0.3 percent by weight.

* * * * *